(12) United States Patent
Ozarowski et al.

(10) Patent No.: US 6,488,623 B1
(45) Date of Patent: Dec. 3, 2002

(54) SKIN PERFUSION EVALUATION APPARATUS

(75) Inventors: Ryszard S. Ozarowski, Marietta, GA (US); William T. Sutton, Charleston, SC (US)

(73) Assignee: Hill-Rom Services, Inc., Batesville, IN (US)

(*) Notice: Subject to any disclaimer, the term of this patent is extended or adjusted under 35 U.S.C. 154(b) by 71 days.

(21) Appl. No.: 09/710,325

(22) Filed: Nov. 9, 2000

(51) Int. Cl.$^7$ ................................................ A61B 5/00
(52) U.S. Cl. ....................... 600/363; 600/306; 600/504
(58) Field of Search .................................. 600/306, 363, 600/504, 549; 601/15; 606/20; 607/96, 98, 99, 108, 112; 374/10–13, 44; 73/204.11

(56) References Cited

U.S. PATENT DOCUMENTS

| | | | |
|---|---|---|---|
| 2,591,443 A | 4/1952 | Larson et al. | ................ 600/482 |
| 2,855,920 A | 10/1958 | Parrot | ......................... 600/482 |

(List continued on next page.)

FOREIGN PATENT DOCUMENTS

| | | |
|---|---|---|
| DE | 27 37 709 A1 | 3/1979 |
| DE | 33 09 093 A1 | 9/1984 |
| EP | 0 019 478 A2 | 11/1980 |
| EP | 0 136 881 | 4/1985 |

OTHER PUBLICATIONS

P. Svedman, et al., "A Device for Noninvasive Assessment of Perfusion Pressure in the Skin of Healthy Volunteers", Journal of Investigative Surgery, vol. 2, pp. 479–485, 1989.

H. B. Stoner, et al., "Relationships between skin temperature and perfusion in the arm and leg", Clinical Physiology, pp. 27–40, 1991.

L. Bennett, et al., "Vertical Shear Existence in Animal Pressure Threshold Experiments", Decubitus, vol. 1, No. 1, pp. 18–24, Feb. 1988.

G. Pye, et al., "Skin temperature as an indicator of stress in soft tissue", Engineering in Medicine, vol. 5, No. 3, 1976, pp. 58–60.

J. H. Meijer, et al., "Method for the measurement of susceptibility to decubitus ulcer formation", Medical & Biological Engineering & Computing, vol. 27, No. 5, Sep. 1989, pp. 502–506.

P. Svedman, et al., "Epithelialization and Blood Flow in Suction Blister Wounds on Healthy Volunteers", Investigation Surgery, vol. 4, pp. 175–189, 1991.

Julia Anne Ablarde, Queen's thesis, "Skin Vascular Response to Normal Mechanical Forces", Jul. 1992.

(List continued on next page.)

*Primary Examiner*—Kevin Shaver
*Assistant Examiner*—Charles Marmor, II
(74) *Attorney, Agent, or Firm*—Barnes & Thornburg

(57) ABSTRACT

The disclosure relates to a device for determining perfusion capacity in a region of a patient's skin and underlying tissue utilizing a thermoelectric device to create a temperature differential, a sensor for measuring the temperature differential, a controller coupled to the sensor and the thermoelectric device for maintaining the temperature differential substantially constant by providing electrical energy to the thermoelectric device, and measuring the electrical energy provided to the thermoelectric device when the thermoelectric device is positioned adjacent the region of the patient's skin to indicate perfusion capacity.

33 Claims, 7 Drawing Sheets

U.S. PATENT DOCUMENTS

| | | | |
|---|---|---|---|
| 3,291,120 A | 12/1966 | Karakashian | 600/482 |
| 3,302,636 A | 2/1967 | Clemetson | 600/482 |
| 3,338,090 A | 8/1967 | Coombs, Jr. et al. | 600/403 |
| 3,570,312 A | 3/1971 | Kreith | 374/183 |
| RE30,317 E | 7/1980 | Lübbers et al. | 600/363 |
| 4,230,122 A | 10/1980 | Lübbers et al. | 600/357 |
| 4,267,844 A | 5/1981 | Yamanishi | 600/315 |
| 4,306,569 A | 12/1981 | Weil et al. | 600/549 |
| 4,354,504 A * | 10/1982 | Bro | 600/504 |
| 4,425,921 A | 1/1984 | Fujisaki et al. | 600/503 |
| 4,475,554 A | 10/1984 | Hyndman | 600/473 |
| 4,523,597 A | 6/1985 | Sawa et al. | 600/405 |
| 4,538,618 A | 9/1985 | Rosenberg et al. | 600/407 |
| 4,554,930 A | 11/1985 | Kress | 600/587 |
| 4,585,002 A * | 4/1986 | Kissin | 607/96 |
| 4,677,985 A * | 7/1987 | Bro et al. | 600/504 |
| 4,693,255 A | 9/1987 | Beall | 600/431 |
| 4,699,149 A | 10/1987 | Rice | 600/475 |
| 4,723,554 A | 2/1988 | Oman et al. | 600/306 |
| 4,817,622 A | 4/1989 | Pennypacker et al. | 600/473 |
| 4,859,078 A | 8/1989 | Bowman et al. | 374/44 |
| 4,877,034 A | 10/1989 | Atkins et al. | 600/475 |
| 4,894,547 A | 1/1990 | Leffell et al. | 250/461.2 |
| 5,054,487 A | 10/1991 | Clarke | 600/316 |
| 5,054,502 A | 10/1991 | Courage | 600/587 |
| 5,097,828 A * | 3/1992 | Deutsch | 607/104 |
| 5,243,982 A | 9/1993 | Möstl et al. | 600/316 |
| 5,247,940 A | 9/1993 | Wilk | 600/549 |
| 5,628,769 A * | 5/1997 | Saringer | 607/98 |
| 5,769,784 A | 6/1998 | Barnett et al. | 600/300 |
| 5,800,490 A * | 9/1998 | Patz et al. | 607/108 |
| 6,010,455 A | 1/2000 | Barnett et al | 600/363 |
| 6,017,337 A * | 1/2000 | Pira | 606/20 |
| 6,268,595 B1 * | 7/2001 | Haenel | 219/528 |

\* cited by examiner

SKIN PERFUSION EVALUATION APPARATUS

BACKGROUND AND SUMMARY OF THE INVENTION

The present invention relates to a skin perfusion evaluation apparatus and method. More particularly, the present invention relates to an apparatus and method for rapidly assessing microvascular perfusion of the skin which is capable of providing an indication of vascular sufficiency in the tested area.

The apparatus of the present invention is particularly effective in early detection of pressure ulcers to permit treatment before such pressure ulcers (i.e. bed sores) develop. When a patient is bedridden, soft tissue is often compressed for a long period of time between a bone of the patient and a firm surface such as a mattress. This can cause a localized area of tissue necrosis also known as a pressure ulcer, decubitus ulcer, or bed sore.

It is known that temperature of the skin resulting from intrinsic or non-environmental factors is primarily produced by blood perfusion. The present invention provides a handheld mechanism for rapidly assessing perfusion of the skin. By determining the likelihood for development of pressure ulcers before the pressure ulcers actually occur, it is possible to take preventative steps to prevent pressure ulcers. For instance, the patient could be transferred to a different bed which reduces pressure on the body. The patient can be monitored more closely to make sure that pressure on a particularly vulnerable area is avoided. Therefore, by providing rapid assessment of microvascular perfusion in a particular area, the present invention can reduce the likelihood of development of pressure ulcers, thereby reducing pain and suffering to the patient and reducing costs associated with treating pressure ulcers after they develop.

The apparatus and method of the present invention is also useful for diabetics. The apparatus and method for evaluating skin perfusion can be used to monitor and detect vascular insufficiency in the legs before the insufficiencies lead to leg ulcers and other problems. The apparatus and method of the present invention is useful in any instance where determination of reduced blood flow in an area can result in earlier treatment (i.e. tissue flaps and grafts).

According to one aspect of the present invention, an apparatus is provided for evaluating perfusion adjacent a skin surface. The apparatus includes a thermoelectric device having a cold plate and a hot plate with a temperature differential therebetween. The thermoelectric device is mounted so that it can be positioned adjacent the region of the patient's skin. The device includes a sensor for measuring the temperature differential between the cold plate and the hot plate and a controller coupled to the sensor in the thermoelectric device for maintaining the temperature differential substantially constant by providing electrical energy to the thermoelectric device. The electrical energy provided to the thermoelectric device when it is positioned adjacent the region of the patient's skin is indicative of the perfusion capacity. Additionally, the cold plate may be positioned to lie between the patient's skin and the hot plate when the thermoelectric device is positioned adjacent the region of the patient's skin. A heat sink may be provided for maintaining the hot plate at the temperature substantially equal to the temperature of ambient air. The thermoelectric device may be a Peltier device. The device may include a DC power source electrically coupled to the thermoelectric device, and a gauge for measuring the electrical energy provided to the thermoelectric device.

According to another aspect of the present invention, a device for determining a perfusion capacity in a region of a patient's skin and underlying tissue includes a plate mounted in a position permitting placement of the plate adjacent the region of the patient's skin. A sensor is provided to determine the temperature of the plate and a controller is coupled to the sensor and to the plate to provide electrical energy to the plate to maintain the temperature of the plate substantially constant. The electrical energy provided to the plate when the plate is positioned adjacent the region of the patient's skin is indicative of the perfusion capacity in the region of the patient's skin and underlying tissue. The device may include a gauge coupled to the controller for measuring the energy required to maintain the temperature of the plate substantially constant. The device may also include a second plate spaced apart from and thermally coupled to the first plate by a boundary so that providing electrical energy to the first and second plates induces heat to cross the boundary between the first plate and the second plate. A heat sink may be provided for dissipating heat transferred from the first plate to the second plate so as to maintain the temperature of the second plate at the temperature of the ambient air.

According to yet another aspect of the present invention, a device for determining perfusion capacity at a region of the patient's skin and underlying tissue includes a first plate mounted to be placed in a position adjacent the region of the patient's skin and a second plate electrically coupled to the first plate by a junction containing material dissimilar to one of the first and second plates. A controller maintains a first plate at a first temperature and the second plate at a second temperature defining a temperature differential which is maintained substantially constant by the controller by adjusting electrical energy supplied to the first and second plates. The electrical energy supplied to the first and second plates when the first plate is positioned adjacent the region of the patient's skin is indicative of the perfusion capacity of the region of the patient's skin and underlying tissue. The device may include a heat exchanger which maintains the second plate at the temperature of ambient air. A fan can be provided to force ambient air across the heat exchanger. The device may include a power source providing direct current flowing between the first and second plates, which current may flow in the direction which induces the first plate to have a temperature lower than the temperature of the second plate.

According to another aspect of the present invention, a method is provided for evaluating microvascular perfusion adjacent a skin surface. The method includes a step of thermally coupling a plate to a region of the patient's skin and providing energy to the plate to dissipate heat absorbed by the plate from the skin. The provided energy is measured and used to calculate the perfusion capacity. The method may include the step of establishing an initial temperature of the plate before thermally coupling the plate to the region of the patient's skin. This initial temperature may be lower than the temperature of the ambient air adjacent the patient's skin. The method may include providing electrical energy so as to substantially dissipate all of the heat absorbed by the first plate. This energy may be provided until the rate at which the energy is provided reaches a steady state value.

According to yet another aspect of the present invention, a method for using a first plate and a second plate and the differential temperature therebetween to determine the perfusion capacity of a region of a patient's skin and underlying tissue utilizes plates that are juxtaposed and configured such that heat applied to the first plate relative to the second plate will provide an electrical measurement. The method includes placing the first plate adjacent to the region of the patient's skin, providing an electrical measurement indicative of the energy affecting the differential temperature, and providing an indication of the perfusion capacity related to the energy affecting the differential temperature. The energy affecting the differential temperature may be an energy required to maintain the differential temperatures substantially constant. The method may also include the step of allowing the energy affecting the differential temperature to reach a steady state value after the first plate is placed adjacent to the region of the patient's skin. The method may also include the step of maintaining the second plate at a substantially constant temperature.

According to still another aspect of the present invention, a method for using the Peltier Effect ("PE") to determine a perfusion capacity of a region of the patient's skin and underlying tissue includes steps of providing a PE sensor having a first plate to be thermally coupled to the region of the patient's skin and a second plate spaced apart from the first plate and a controller for applying a current across the plates. The first plate is thermally coupled to the patient's skin and the current required to maintain the temperature of the first plate at a setpoint temperature is measured. The current measurement is used to provide an indication of the perfusion capacity. The method may include the step of cooling the first plate to the setpoint temperature which is lower than the expected temperature of the region of the patient's skin by applying a current to the plates prior to thermally coupling the first plate to the region of the patient's skin. The method may also include the step of measuring the current required to maintain the temperature of the first plate at the setpoint temperature to determine a baseline current value prior to thermally coupling the first plate to the region of the patient's skin. The method may also include the step of permitting the measured current to reach a substantially steady state value after thermally coupling the first plate to the region of the patient's skin and comparing the substantially steady state value of the measured current to the baseline current value to provide an indication of perfusion capacity. The thermal coupling of the first plate to the region of the patient's skin may be maintained until the substantially steady state current value is compared to the baseline current value.

Additional features and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF DRAWINGS

Figure 1:
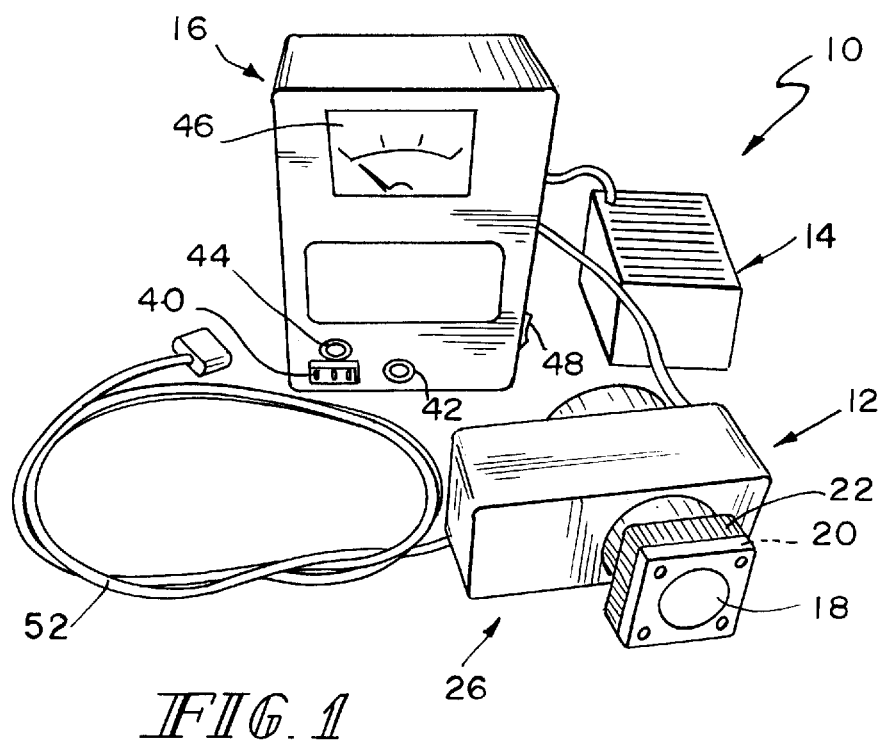
FIG. 1 is perspective view of a thermoelectric skin perfusion evaluation device in accordance with the present invention having a main unit, a power supply, and thermoelectric probe.
Figure 2:
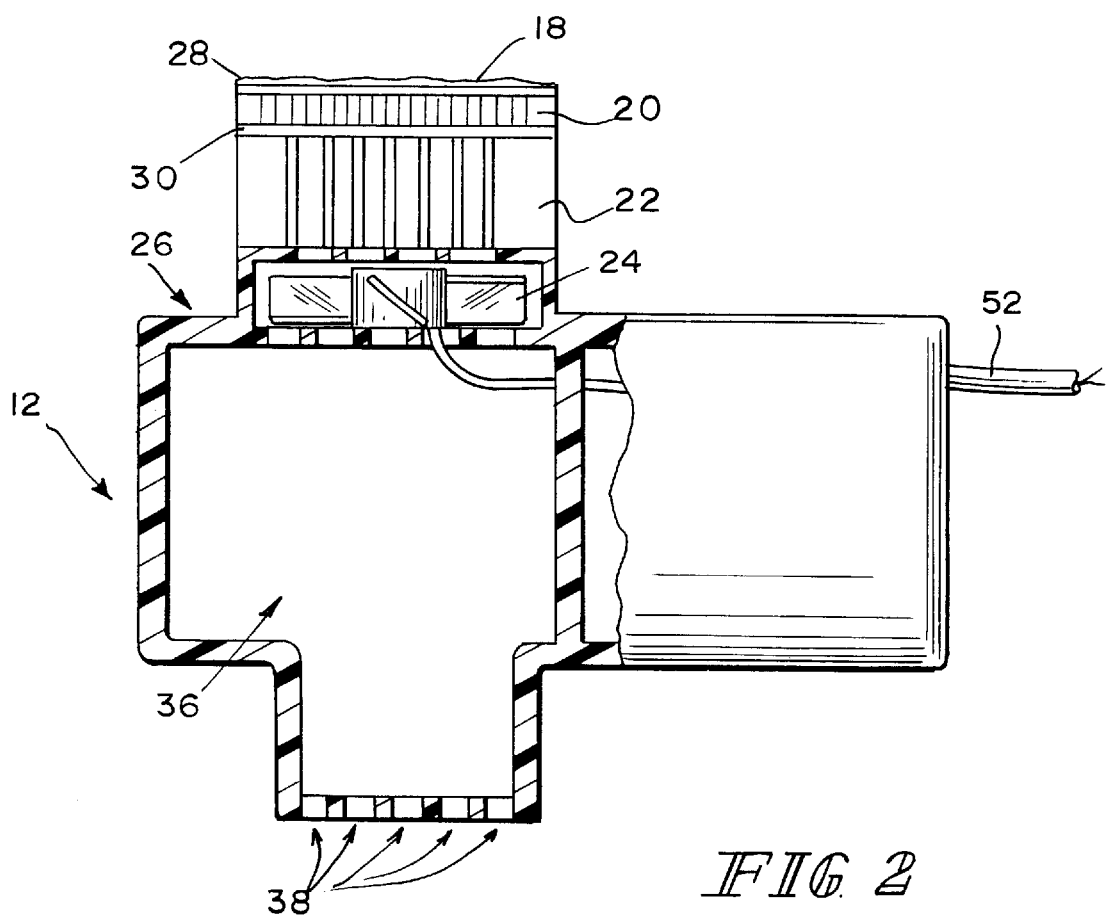
FIG. 2 is partial sectional view of the thermoelectric probe of FIG. 1 showing a patient interface at the top of the figure with a thermoelectric device mounted adjacent thereto having one plate engaging the patient interface and the other plate engaging a heat exchanger which is maintained at the ambient air temperature by a fan.

Referring to FIGS. 1–5 there is illustrated a thermoelectric skin perfusion evaluation apparatus 10 of the present invention. Thermoelectric skin perfusion evaluation device 10 includes a thermoelectric probe 12, a power supply 14, and a main unit 16. Other skin perfusion evaluation devices are disclosed in U.S. application Ser. No. 09/476,837 filed Jan. 3, 2000, and now U.S. Pat. No. 6,248,066, U.S. application Ser. No. 09/102,160 filed Jun. 22, 1998, and U.S. Pat. No. 5,769,784, the disclosure of which are incorporated herein by reference. Thermoelectric skin perfusion evaluation device 10 provides a measurement of the static heat flow through the skin and heat conduction below the skin surface of the patient providing deep tissue measurements. Skin perfusion evaluation apparatus 10, and each of the devices disclosed in the incorporated applications and patent, provide an external stimulus to the skin of the patient which induces a change in the skin surface temperature. Because the surface of a patient's skin has a certain temperature which is maintained by blood flowing through capillaries under it, the reaction of the skin temperature to the external stimulus provides an indication of microcapillary perfusion.

In thermoelectric skin perfusion evaluation device 10 of the present invention, the external stimulus is in the form of contacting the body of a patient with an instrument at a different temperature than the skin causing a local change of the skin surface temperature. When a patient's skin is contacted with an external instrument which is colder than the patient's normal skin temperature, heat is transferred from the patient's skin surface to the instrument in an attempt to reach thermal equilibrium as a result of reducing the skin temperature and increasing the instrument temperature. However, microcapillary flow of blood in the patient's skin tends to maintain the skin temperature at a constant temperature. When energy is applied to the instrument to maintain it at a constant temperature, the energy required to maintain the instrument at the constant temperature is indicative of the heat provided by the microcapillary blood flow or blood perfusion of the skin. Healthy skin with proper perfusion provides greater heat transfer from the skin to the instrument resulting in more energy having to be added to the instrument to maintain the instrument at a constant temperature. When the instrument is in contact with skin with diminished perfusion, less energy is required to maintain the instrument at its initial temperature. Such diminished perfusion may be an indication of illness.

In the illustrated embodiment of the thermoelectric skin perfusion evaluation device 10 of the present invention, the thermoelectric probe 12 includes a patient interface 18, a thermoelectric element 20, a heat exchanger 22, a fan 24, and a housing 26. In the illustrated thermoelectric probe 12, thermoelectric element 20 is a Peltier device, also known as a Peltier heat pump, having a cold plate 28 and a hot plate 30. A cold plate sensor 32 is thermally coupled to cold plate 28 and electrically coupled to control circuitry in main unit 16 as is described hereafter. Illustratively, cold plate sensor 32 is a thermistor. A hot plate sensor 34 is thermally coupled to hot plate 30 and electrically coupled to control circuitry 50 contained in main unit 16 as is described later. Illustratively, hot plate sensor 34 is a thermistor. While described as thermistors, it is within the scope of the invention as presently perceived for cold plate sensor 32 and hot plate sensor 34 to be any standard thermoelectric sensor providing an electrical signal indicative of a temperature.

Figure 3:
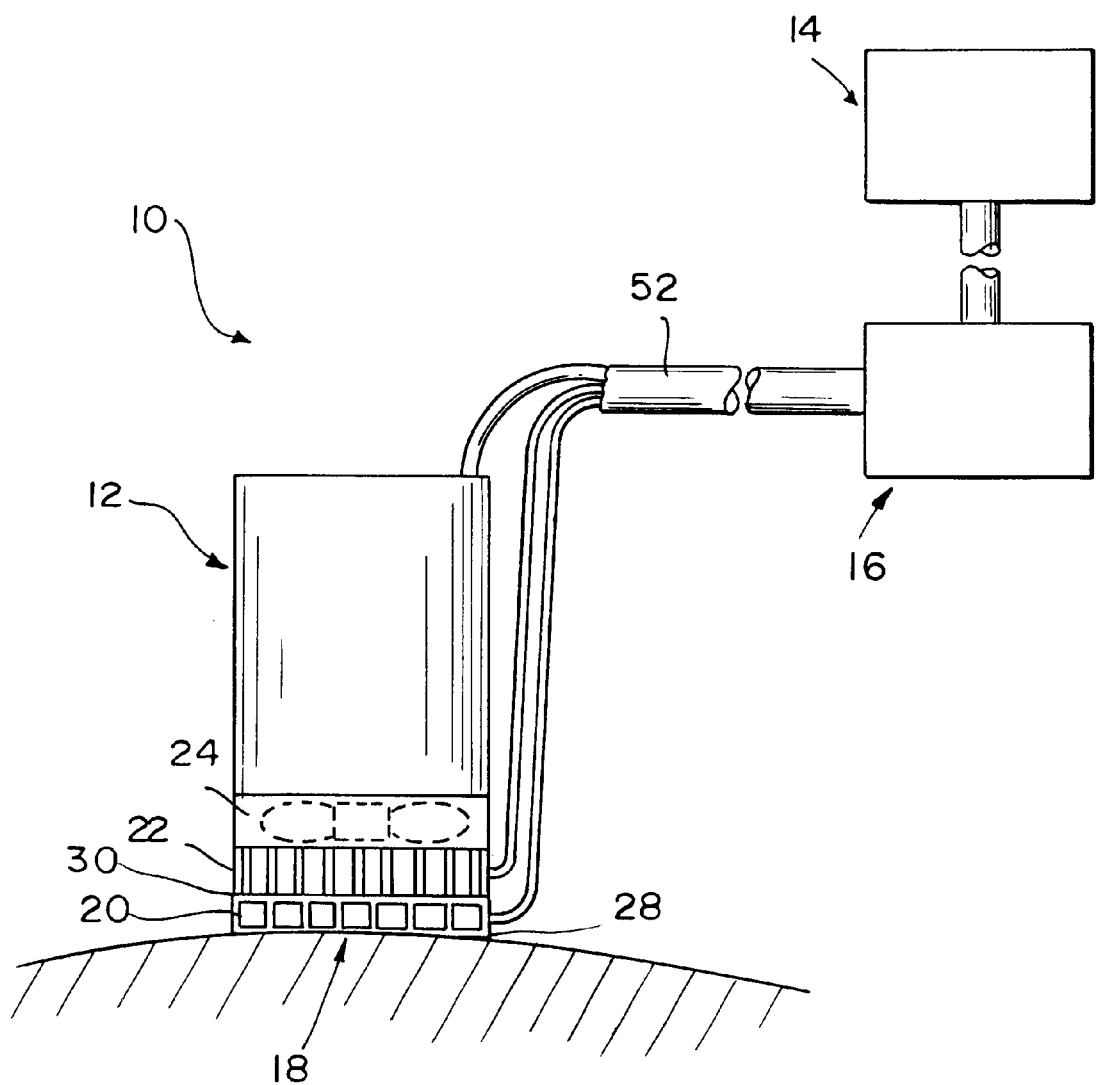
FIG. 3 is a diagrammatic sectional view of the thermal probe and the main unit of the thermoelectric skin perfusion evaluation device of FIG. 1 showing the thermoelectric probe in engagement with a patient's body.

Patient interface 18, thermoelectric element 20, heat exchanger 22, and fan 24 are all mounted in housing 26 as illustrated, for example, in FIG. 3. Patient interface 18 is mounted on an external surface of housing 26. Thermoelectric element 20 is mounted in housing 26 so that cold plate 28 abuts patient interface 18 and is between patient interface 18 and hot plate 30 of thermoelectric element 20. Heat exchanger 22 is mounted in housing 26 to abut and be thermally coupled to hot plate 30 of thermoelectric element 20. Fan 24 is mounted in housing 26 adjacent to heat exchanger 22 so that fan 24 can force ambient air over heat exchanger 22 to maintain heat exchanger 22 at approximately the temperature of the ambient air temperature ($T_a$). Housing 26 is formed to include an air chamber 36 communicating with an opening 38 extending through the housing 26 and also communicating with fan 24 so that fan 24 is provided with a source of air at ambient temperature ($T_a$).

As previously mentioned, the preferred thermoelectric element 20 is a Peltier device. Peltier devices operate taking advantage of the Peltier effect. The Peltier effect occurs whenever electrical current flows through a junction between two dissimilar conductors resulting in heat either being absorbed or released at the junction. Thus, Peltier devices can be used as heat pumps operating in either a refrigeration cycle or a heating cycle. When used in the refrigeration cycle, the cold plate 28 is placed adjacent an object to be cooled and the hot plate 30 is placed adjacent a heat sink such as heat exchanger 22 and fan 24. Peltier devices operate on direct current (DC) so that by changing polarity of the current, the Peltier device can be configured to operate either in a refrigeration or a heating cycle.

When there is no heat flux into the object adjacent to the cold plate 28, heat flows across the boundary between the object to be cooled and the cold plate 28. Providing properly polarized current to the Peltier device 20 causes heat to flow from cold plate 28 through the junction to the hot plate 30 and across the boundary between the hot plate 30 and the heat exchanger 22. As a result, heat flows away from the object and the object is eventually cooled. However, when there is heat entering the object to be cooled, such as heat being carried by blood as a result of microcapillary perfusion, the object adjacent the cold plate 28 may reach a dynamic equilibrium temperature with the cold plate 28. By maintaining the hot plate 30 at a constant temperature, current flowing into the Peltier device 20 maintains the cold plate 28 at a constant temperature so that there is a constant temperature differential between the cold plate 28 and the hot plate 30. The energy required to maintain this temperature differential is indicative of the heat flux of the skin resulting from microcapillary perfusion. The disclosed thermoelectric skin perfusion evaluation device 10 operates on this principle.

Thermoelectric skin evaluation device 10 is used to evaluate skin perfusion by placing patient interface 18 of thermoelectric probe 12 in contact with the patient's body. Cold plate 28 is adjacent to, and thereby thermally coupled through patient interface 18 with, the region of the patient's skin which is contacted by patient interface 18. See FIGS. 6–8, steps 156, 194, 232. Hot plate 30 is maintained substantially at ambient air temperature by heat exchanger 22 and fan 24. See FIG. 7, step 196. The temperature of hot plate 30 is measured by hot plate sensor 34 and a signal proportional to that temperature is sent to control circuitry as described later. Since cold plate 28 is thermally coupled through patient interface 18 to the patient's skin surface, heat crosses the boundary between the patient's skin surface and the cold plate 28. This heat transfer would induce the temperature of cold plate 28 to increase if no current is provided to the Peltier device 20. However, in the illustrated invention, current is provided to the Peltier device 20 to maintain the temperature differential between the hot plate 30 and the cold plate 28 when the cold plate 28 is in contact with the patient's skin. See FIG. 7, step 198. The temperature of cold plate 28 is measured by cold plate sensor 32 which sends a signal proportional to the temperature to control circuitry 50 as described later. The energy required to maintain the differential temperature between the hot plate 30 and cold plate 28 is indicative of the heat flow induced by contact between probe 12 and the patient's body. See FIG. 7, step 204.

In the illustrated thermoelectric probe 12, thermoelectric element 20 is a 1"×1" Peltier device available from Ferrotech America Corporation. See FIG. 8, step 222. Heat exchanger 22 is an aluminum heat sink integral with fan 24, which is a cooling fan commonly used for cooling Pentium Processors and is available from Radio Shack. Heat exchanger 22 and fan 24 approximate a heat reservoir at ambient air temperature ($T_a$) forming a boundary with hot plate 30 to maintain hot plate 30 at substantially ambient air temperature ($T_a$). See FIG. 7, step 196.

Thermoelectric skin perfusion evaluation device 10 provides an indication of the heat flow between the cold plate 28 of the thermoelectric probe 12 and the patient's body. Device 10 stabilizes the temperature difference between the ambient air and the cold plate 28 of the probe 12. The steady state current provided to the thermoelectric element 20 when in contact with the patient's body is indicative of the heat flow induced by the contact of the probe 12 with the patient's body which is indicative of microvascular perfusion in the region of contact between probe 12 and the patient's body. See FIGS. 6–8, steps 166, 204, 242.

As mentioned previously, Peltier devices operate using direct current. Therefore, power supply 14 is a DC power supply providing direct current. Illustratively, power supply 14 is a commercially available 12V, 1500 mA power supply. The DC power supplied by power supply 14 supplies the thermoelectric probe fan 24, thermoelectric element 20, and support electronics 50 contained in main unit 16.

Main unit 16 includes a thermoelectric probe connector 40, power supply connector 42, BNC output connector 44, output gauge 46, on/off switch 48, and support electronics 50. Thermoelectric probe connector 40 provides electrical coupling between thermoelectric probe 12 and main unit 16 via cable 52. Cable 52 carries signals from cold plate sensor 32 and hot plate sensor 34 to support electronics 50 in main unit 16. Cable 52 also carries power from power supply 14 through main unit 16 to thermoelectric element 20 and fan 24 in thermoelectric probe 12.

Referring to FIGS. 4(*a*) and 4(*b*), support electronics 50 are illustrated. Illustratively, except for cold plate sensor 32, hot plate sensor 34, and Peltier device 20, which are contained in probe 12, and V$_{cc}$ and ground which are contained in power supply 14, most of the components of support electronics 50 are housed in main unit 16. Cold plate sensor or thermistor 32 and hot plate sensor or thermistor 34 are connected in a bridge scheme with resistors 54, 56 and potentiometer 58, as shown in FIG. 4(*a*). The diagonal of the bridge is connected to an instrumentation amplifier 60 having a very high input resistance.

Instrumentation amplifier 60 includes a first stage 62, a second stage 78, and a third stage 84. First stage 62 includes field effect transistor operational amplifiers 64 and 66 coupled at the non-inverting inputs (+) to the diagonal of the bridge as shown for example in FIG. 4(*a*). As shown, for example, in FIG. 4(*a*), op-amp 64 receives a signal influenced by hot plate sensor 34 and op-amp 66 receives a signal affected by cold plate sensor 32. The inverting inputs (−) of the field effect transistor amplifiers 64, 66 are coupled to feedback loops of the output signals running through feedback resistors 68 and 70 respectively. Non-inverting inputs of field effect transistor amplifiers 64 and 66 are also coupled to the sliding contact 72 and an end contact 74 of potentiometer 76 respectively as shown, for example, in FIG. 4(*a*).

Illustratively, field effect transistor amplifiers 64 and 66 are contained on single integrated circuit J-FET dual operational amplifier TL082 available from Texas Instruments, Inc. available in an eight pin package. Pin 8 and ground pin 4 provide power to both amplifier 64, 66. Inverting inputs are available on pins 2 and 6 for operational amplifiers 64, 66, respectively. Non-inverting inputs are available on pins 3 and 5 for operational amplifiers 64, 66, respectively. Outputs of operational amplifiers 64, 66 are on pins 1 and 7 respectively of the integrated circuit.

Second stage 78 of instrumentation amplifier 60 includes a differential amplifier 80 and an amplifier 82 providing a virtual ground signal to the non-inverting input of differential amplifier 78 to reject common mode bias or noise. The second stage 78 of instrumentation amplifier 60 provides a single ended temperature differential signal to third stage 84 of instrumentation amplifier 60. The second stage 78 of instrumentation amplifier 60 receives an amplified signal proportional to the hot plate 30 temperature from the output of amplifier 64 and an amplified signal proportional to the temperature of cold plate 28 from the output of amplifier 66. The amplified hot plate temperature signal is coupled to a first contact of resistor 86 which is coupled at its second contact to the non-inverting input of operational amplifier 88. Non-inverting input of operational amplifier 88 is also coupled through resistor 90 to the virtual ground signal produced by amplifier 82 to reject common mode bias or noise. Amplified cold plate temperature signal is coupled to first contact of resistor 92 which is coupled at second contact to the inverting input of operational amplifier 88. The inverting input of operational amplifier 88 is also coupled through feedback resistor 94 to output signal of operational amplifier 88.

Amplifier 82 generates a virtual ground output used for common mode noise and bias rejection by differential amplifier 80. The non-inverting input of amplifier 82 is coupled to a voltage divider having a first resistor 96 and second resistor 98 dropping the voltage between Vcc and ground. The non-inverting input of amplifier 82 is coupled directly to the output signal of amplifier 82 through a feedback loop, as shown for example, in FIG. 4(*a*). The second stage 78 of instrumentation amplifier 60 generates a single ended temperature differential signal from the output of operational amplifier 88 which is coupled to the third stage 84 of instrumentation amplifier 60.

Illustratively, operational amplifier 88 and amplifier 82 are two of the four operational amplifiers packaged in a 14 pin quad low power operational amplifier LM324 manufactured by Motorola and available from Radio Shack as Catalogue No. 276-1711. Power supply voltage Vcc from power supply 14 is coupled to pin 4 of quad low power operational amplifier package and pin 11 of the package is coupled to ground. Operational amplifier 88 has its inverting input on pin 2, non-inverting input on pin 3, and output on pin 1 of the package. Amplifier 82 has its non-inverting input on pin 5, inverting input on pin 6, and output on pin 7 of the package.

Third stage 84 utilizes the fourth operational amplifier from the quad low power operational amplifier LM324 used in second stage 78 of instrumentation amplifier 60. Third stage 84 amplifies the single ended temperature differential signal output by the second stage 78 of instrumentation amplifier 60. Temperature differential signal is coupled to a first contact of resistor 102 which is coupled at its second contact to the inverting input of operational amplifier 100. Inverting input of operational amplifier 100 is also coupled through a feedback resistor 104 to the output of operational amplifier 100. The non-inverting input of operational amplifier 100 is coupled through resistor 106 to virtual ground. Non-inverting input of operational amplifier 100 is pin 12, inverting input of operational amplifier 100 is pin 13, and output of operational amplifier 100 is pin 14 of the quad low power operational amplifier LM324 previously described. Amplified error signal on the output of operational amplifier 100 represents the output of instrumentation amplifier 60 which is forwarded to a controller 108.

Controller 108 includes a proportional integral controller 110 and a final amplifying stage 112. The proportional stage 114 of PI controller 110 includes an operational amplifier 116, and integral stage 117 of PI controller 110 includes operational amplifier 118. The error signal from instrumentation amplifier 60 is coupled to a first contact of resistor 120 which is coupled at its second contact to non-inverting input of operational amplifier 116 of proportional controller 114. Inverting input of amplifier 116 is also coupled through feedback potentiometer 122 to the output of operational amplifier 116. Non-inverting input of operational amplifier 116 is coupled to virtual ground. Output of operational amplifier 116 is coupled to a first contact of resistor 124 which carries the proportional component of control signal at its second contact.

The integral stage 117 includes operational amplifier 118. The error signal from the output of instrumentation amplifier 60 is coupled at a first contact of potentiometer 126 which is coupled at its second contact to inverting input of operational amplifier 118. The slider of potentiometer 126 is coupled to the inverting input of operational amplifier 118 for adjustment of the integrating time constant. The inverting input of operational amplifier 118 is coupled through integrating feedback capacitor 128 to the output of operational amplifier 118. The non-inverting input of operational amplifier 118 is coupled to virtual ground. The output of operational amplifier 118 is coupled to first contact of resistor 130 which carries at its second contact the integral component of control signal.

Control signal amplification stage 112 of controller 108 includes operational amplifier 132. The proportional component and integral component of control signal are coupled to the inverting input of operational amplifier 132. The inverting input of operational amplifier 132 is also coupled through feedback resistor 134 to the output of operational amplifier 132. Non-inverting input of operational amplifier 132 is coupled through resistor 136 to virtual ground. An amplified control signal is provided on the output of operational amplifier 132 which is applied to an amplifier 138 that drives HEXFET based current sink 142 connected to Peltier device 20.

Amplifier 138 includes an operational amplifier 140. Non-inverting input of operational amplifier 140 is coupled to the output of control signal amplifier 112, as shown for example in FIG. 4(b). The output of operational amplifier 140 of amplifier 138 is coupled to the sink of HEXFET 142. The Peltier device 20, drain and gate of HEXFET 142, and high power resistor 144 are coupled in series between Vcc of the power supply and virtual ground as shown, for example, in FIG. 4(b). The inverting input of operational amplifier 140 of amplifier 138 is coupled to the gate of HEXFET 142.

Operational amplifiers 116, 118, 132, and 140 are four operational amplifiers contained on a single integrated circuit quad low power operational amplifier LM324 manufactured by Motorola and available from Radio Shack, Inc. as Catalogue No. 276-1711. Illustratively, the inverting input of operational amplifier 116 is on pin 2, non-inverting input of operational amplifier 116 is on pin 3 and output of operational amplifier of 116 is on pin 1 of quad operational amplifier. Similarly, non-inverting input of operational amplifier 118 is on pin 5, the inverting input of operational amplifier 118 is on pin 6, and the output of operational amplifier 118 is on pin 7 of the quad operational amplifier. The non-inverting input of operational amplifier 132 is on pin 12, the inverting input of operational amplifier 132 is on pin 13, and the output of operational amplifier 132 is on pin 14 of the quad operational amplifier. The non-inverting input of operational amplifier 140 is on pin 10, the inverting input of operational amplifier 140 is on pin 9 and the output of operational amplifier 140 is on pin 8. Pin 4 is connected to Vcc of the power supply 14 and pin 11 is coupled to virtual ground to provide the power to operational amplifiers 116, 118, 132, and 140 in the controller 108 and amplifier 138.

The output of controller 108 is applied to amplifier 138 which drives the current sink of HEXFET 142 which is connected to Peltier device 20. High power 10 ohm resistor 144 connected in series with the Peltier device 20 is used to measure cooling current since the current flowing through the Peltier device 20 cannot be measured directly in a reliable manner. Thus the current through the Peltier device 20 is equal to the voltage of the current sink input divided by the resistance of source resistor 144.

Figures 4A, 4B:
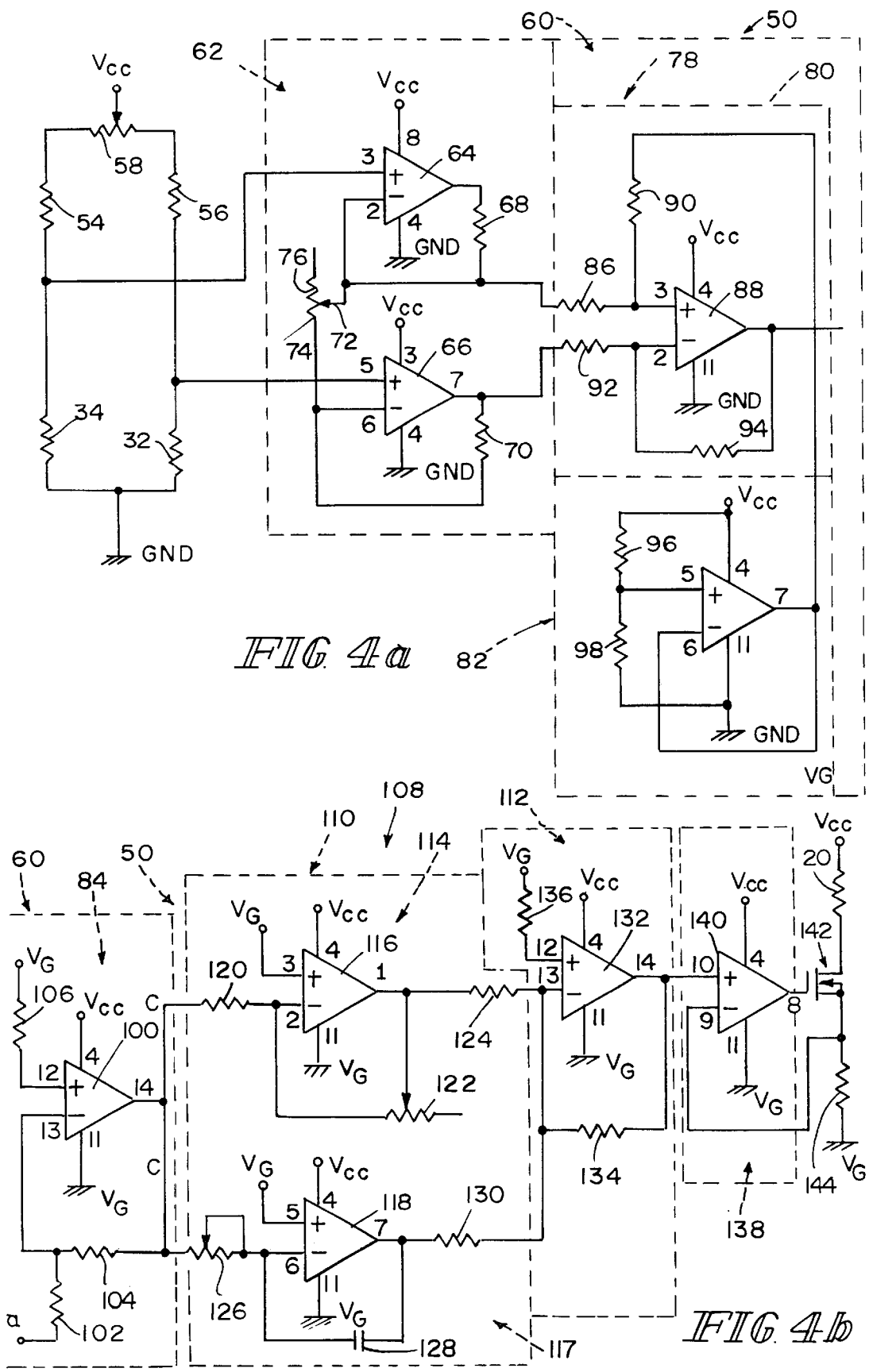
FIGS. 4(a) and 4(b) are simplified schematics of support electronics contained in the power supply, main unit and thermoelectric probe of the thermoelectric device of FIG. 1, most of which are contained in the main unit.

Although not shown in FIGS. 4(a) and 4(b), leads of gauge 46 are connected across contacts of resistor 144 to provide a visual indication of the current flowing through the Peltier device 20. The electronic circuit is adjusted to maintain a practically constant temperature difference between hot plate 30 and cold plate 28. See FIG. 7, step 198. The electronic circuit generates a constant differential temperature between the patient interface 18 and ambient air. The heat exchange between cold plate 28 and still air is low so the current in the Peltier element 20 is at low values until the patient interface 18 is brought into contact with the patient's body, as shown, for example, in FIGS. 5(a) and 5(b) between $t_0$ and $t_1$. Coupling of cold plate 28 to the patient's body through patient interface 18 creates heat flow from the body to the cold plate 28. This flow momentarily increases the temperature of cold plate 28. The electronic circuit increases current in the Peltier device 20 to compensate for this temperature increase and keep the temperature difference between cold plate 28 and hot plate 30 substantially constant. See FIG. 7, step 198.

Figure 5A:
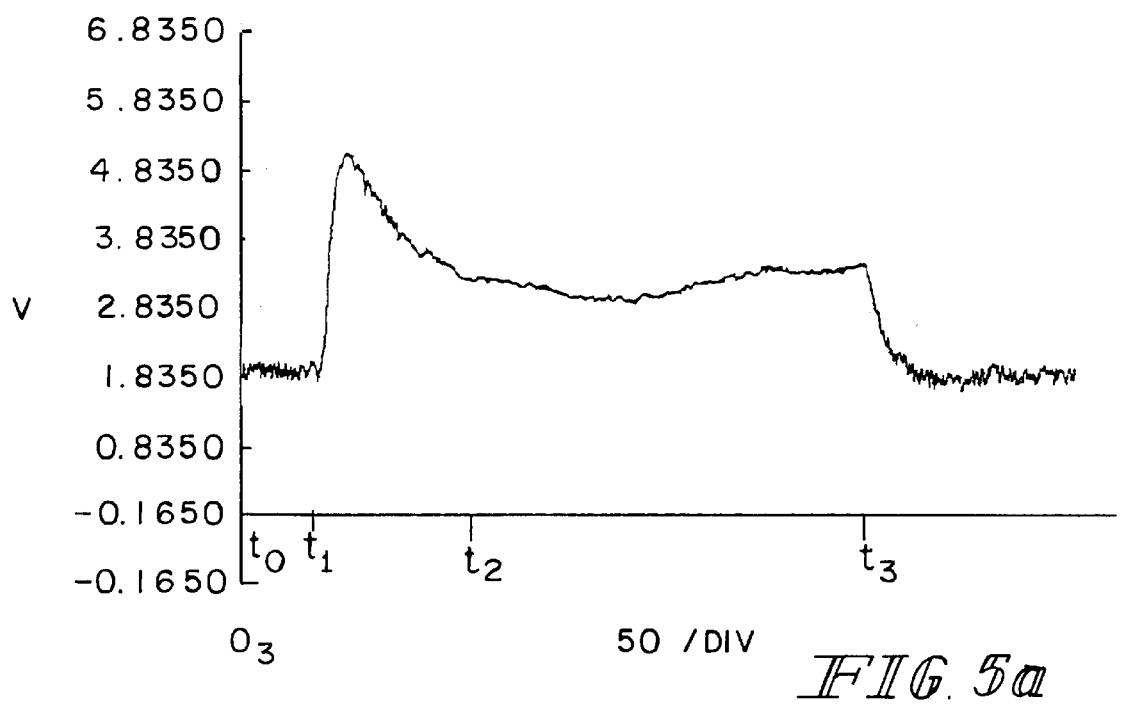
FIGS. 5(a) and 5(b) are plots of the voltage dropped across a source resistor supplying current to the thermoelectric element of the thermoelectric probe of the present invention versus time, the plots show initial and final states in which the probe is in contact with ambient air and intermediate states in which the probe is brought into contact with the patient's body and allowed to come to a steady state condition and then removed from the patient's body.
Figure 5B:
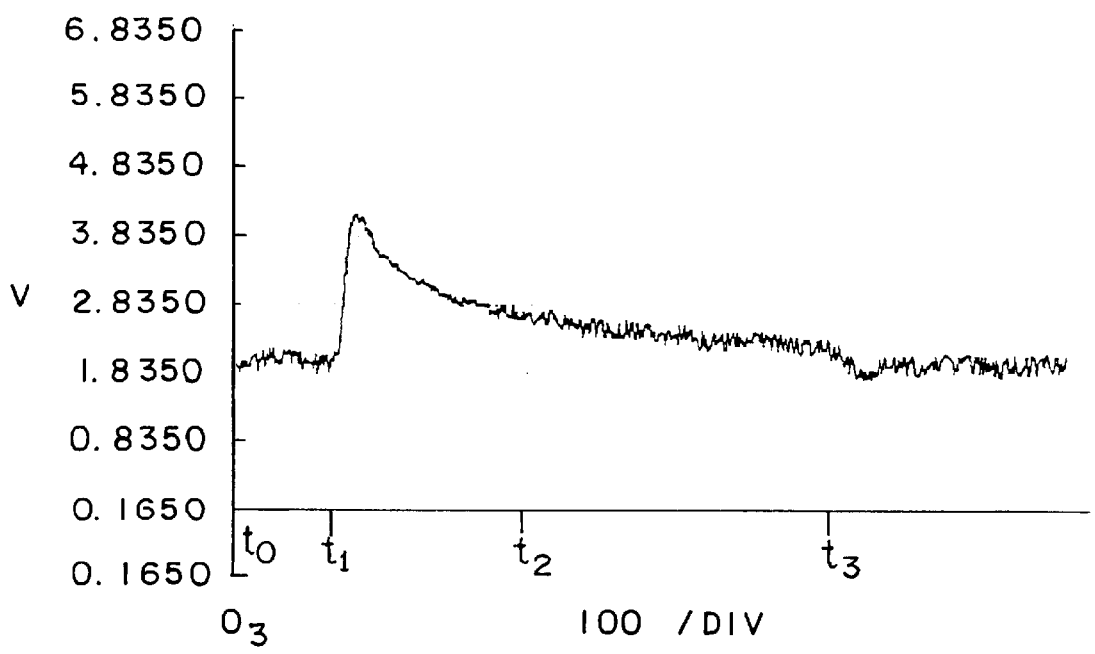

Upon initial contact of the patient interface 18 with the patient's body, shown at time $t_1$ in FIGS. 5(a) and 5(b), the current through the Peltier device 20 rapidly rises. The current initially overshoots the steady state condition but eventually settles into a substantially steady state condition (shown between $t_2$ and $t_3$) wherein the temperature differential between cold plate 28 and hot plate 30 is maintained. See FIGS. 6–8, steps 164, 200, 238. When the patient interface 18 is disconnected from the patient's body (as shown at time $t_3$), the Peltier current returns to its previous level.

Those of ordinary skill in the art will recognize that while the invention has been described as taking advantage of the Peltier effect and using a thermoelectric device 20, it is within the teaching of the invention to use a thermoelectric device 20 and the Seebeck effect to provide an indication of perfusion capacity of a patient's skin. The Seebeck effect is essentially the flip side of the Peltier effect. When thermal energy moves through an electrically conductive material, charge carriers are transported by the heat so that an electrical pressure or voltage is created in a thermoelectric device. A load may be connected to the thermoelectric device to cause current flow which can be measured to provide an indication of skin perfusion.

It will also be understood that while the invention has been described as applying the cold plate 28 to the patient's skin, it is within the teaching of the invention to apply the hot plate 30 to the patient's skin with or without a patient interface 18 therebetween. Also, although the invention has been described with regard to controlling the temperature differential between the hot plate 30 and cold plate 28, it is within the teaching of the invention to control the temperature of the plate in contact with the patient's skin measuring the energy required to control this temperature to provide an indication of skin perfusion capacity.

Figure 6:
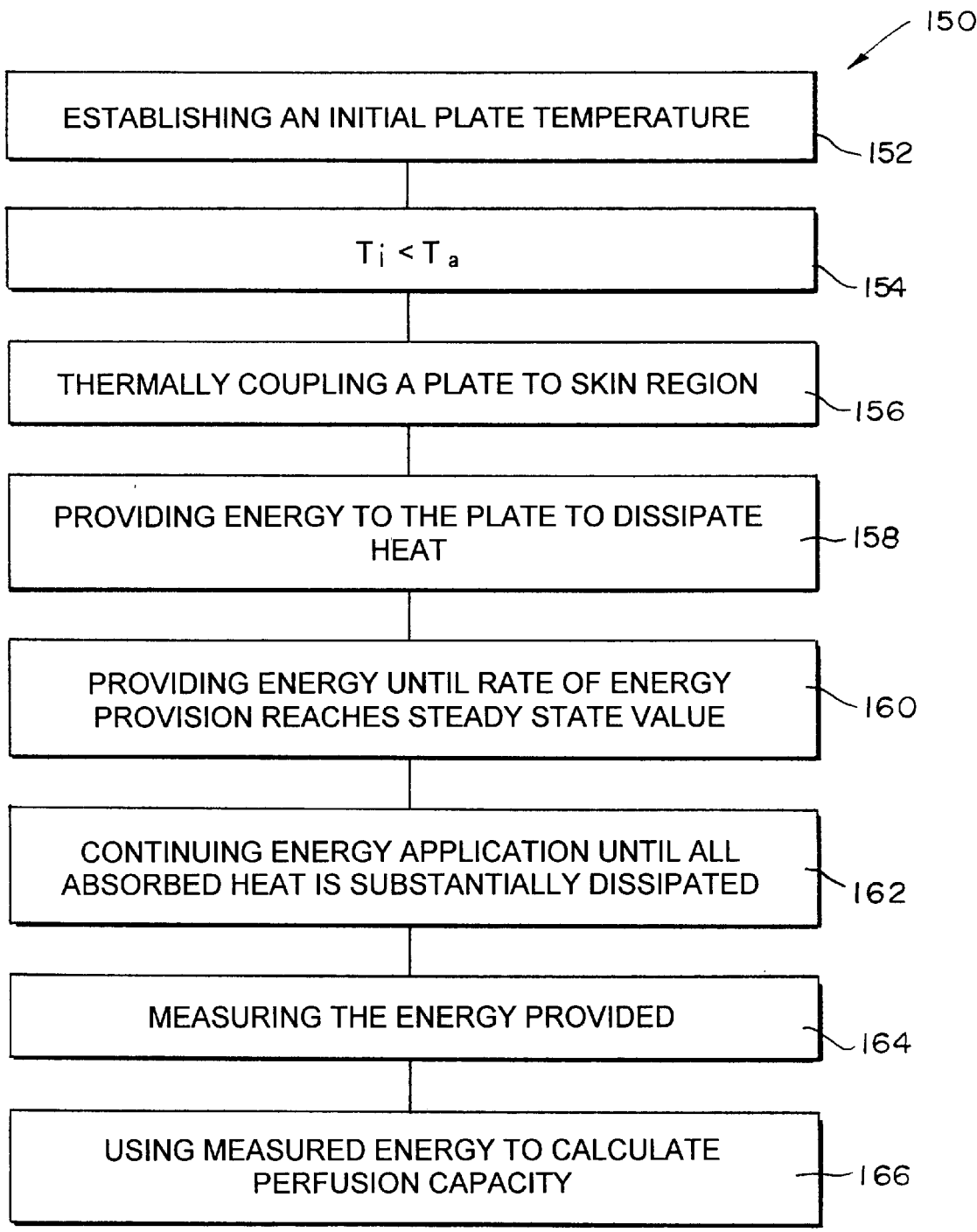
FIG. 6 is a flowchart of the steps of a method of determining perfusion capacity of a region of a patient's skin.

In accordance with another aspect of the invention, a method 150 of determining skin perfusion capacity in a region of a patient's skin and underlying tissue is disclosed in FIG. 6. The method 150 includes the steps of providing an instrument having a plate and establishing the initial temperature of the plate 152 prior to placing the plate adjacent to the region of the patient's skin. When using the device 10 disclosed above, the initial temperature of the plate is established at an initial temperature $T_i$ lower than the ambient air temperature $T_a$ 154. It will be understood that the initial temperature $T_i$ of the plate may be below, at, or above the ambient air temperature $T_a$, and even above the expected skin temperature of the patient within the scope of the disclosure. The plate is thermally coupled to the skin region 156 by placing the plate adjacent the region of the patient's skin. Using the disclosed device 10, patient interface is disposed between the plate and the region of the patient's skin, however, it is within the scope of the invention as presently perceived to thermally couple the plate to the region of the patient's skin in other manners, such as directly applying the plate to the skin region and the like. Upon the plate being coupled to the region of the patient's skin, heat transfer occurs. Energy is provided to the plate to dissipate the heat 158. In using the device 10 disclosed above, this energy is preferably provided until the rate of energy provision reaches a steady state value 160. The energy is provided until all of the absorbed heat is substantially dissipated 162. The energy required to dissipate heat absorbed by the plate is measured 164 and the energy measured is used to calculate the perfusion capacity 166.

Figure 7:
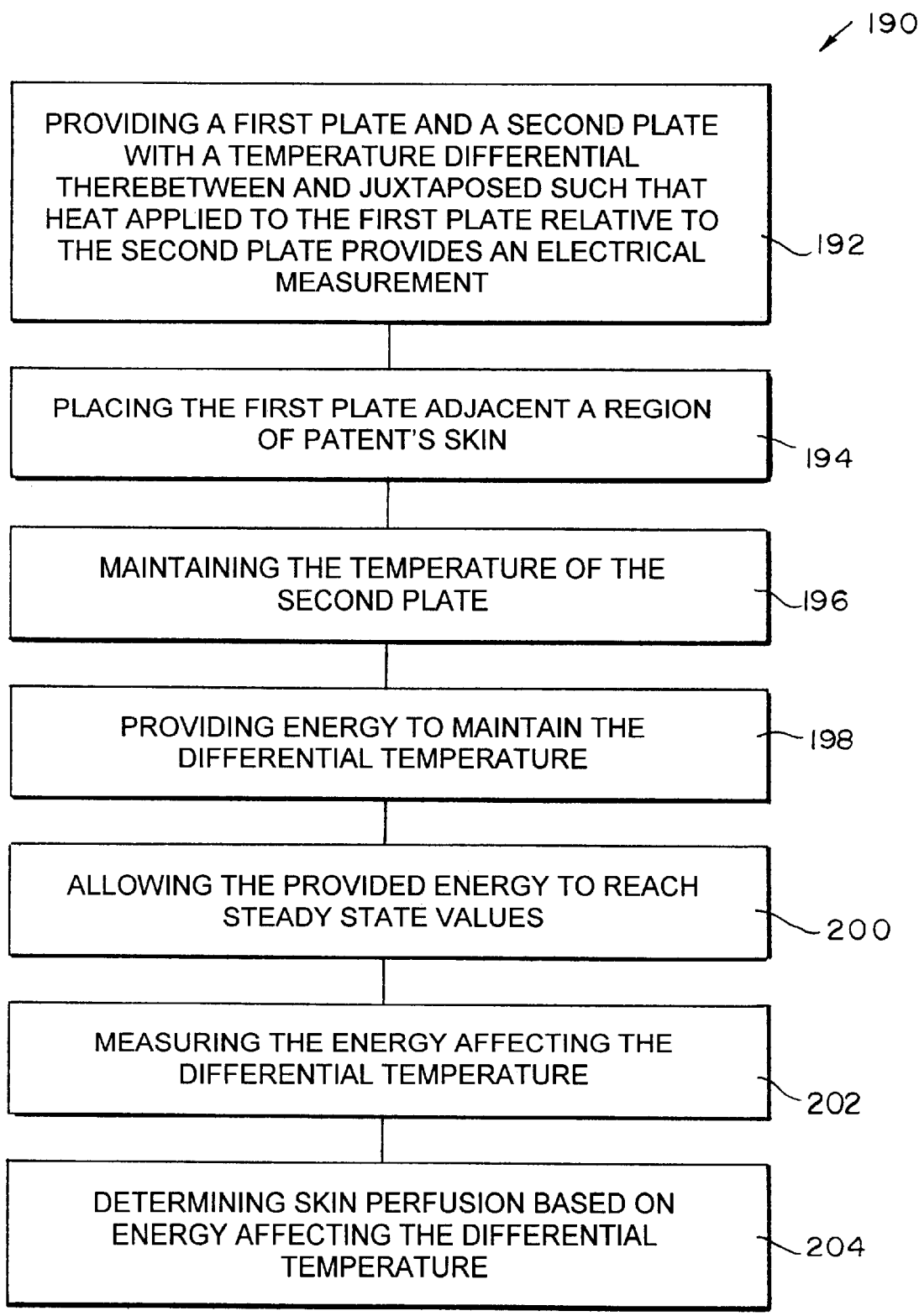
FIG. 7 is a flowchart of the steps of a method of determining perfusion capacity of a region of a patient's skin; and, FIG. 8 is a flowchart of the steps of a method of determining perfusion capacity of a region of a patient's skin.

Another method of determining the skin perfusion capacity of a region of a patient's skin utilizing a first plate and a second plate with a differential temperature therebetween 190 is shown, for example, in FIG. 7. The method 190 includes the step of providing a first plate and a second plate with a temperature differential therebetween and juxtaposed such that heat applied to the first plate relative to the second plate provides an electrical measurement 192. As previously mentioned, a Peltier device 20 may provide an electrical measurement either by the Peltier effect or the Seebeck effect and thus could serve as the provided first and second plate.

The method 190 includes the step of placing the first plate of the provided device adjacent the region of the patient's skin 194. The temperature of the second plate is maintained at a selected temperature 196. Using the device 10 described above in method 190, the temperature of the second plate is maintained at the ambient air temperature $T_a$ by the heat exchanger and fan, however, method 190 is not limited to maintaining the second plate at ambient air temperature. The temperature differential of the first and second plate is maintained by providing energy to the plates 198. When using the device 10 described above, the provided energy is electrical energy. This provided energy is preferably allowed to reach a steady state value 200 to provide an indication of skin perfusion. The energy provided to maintain the temperature differential is measured 202. As shown, for example, in FIGS. 5(*a*) and (*b*), this measurement of energy may be accomplished by measuring the steady state current supplied to a Peltier device 20. Skin perfusion is determined based on the energy affecting the temperature differential 204.

Figure 8:
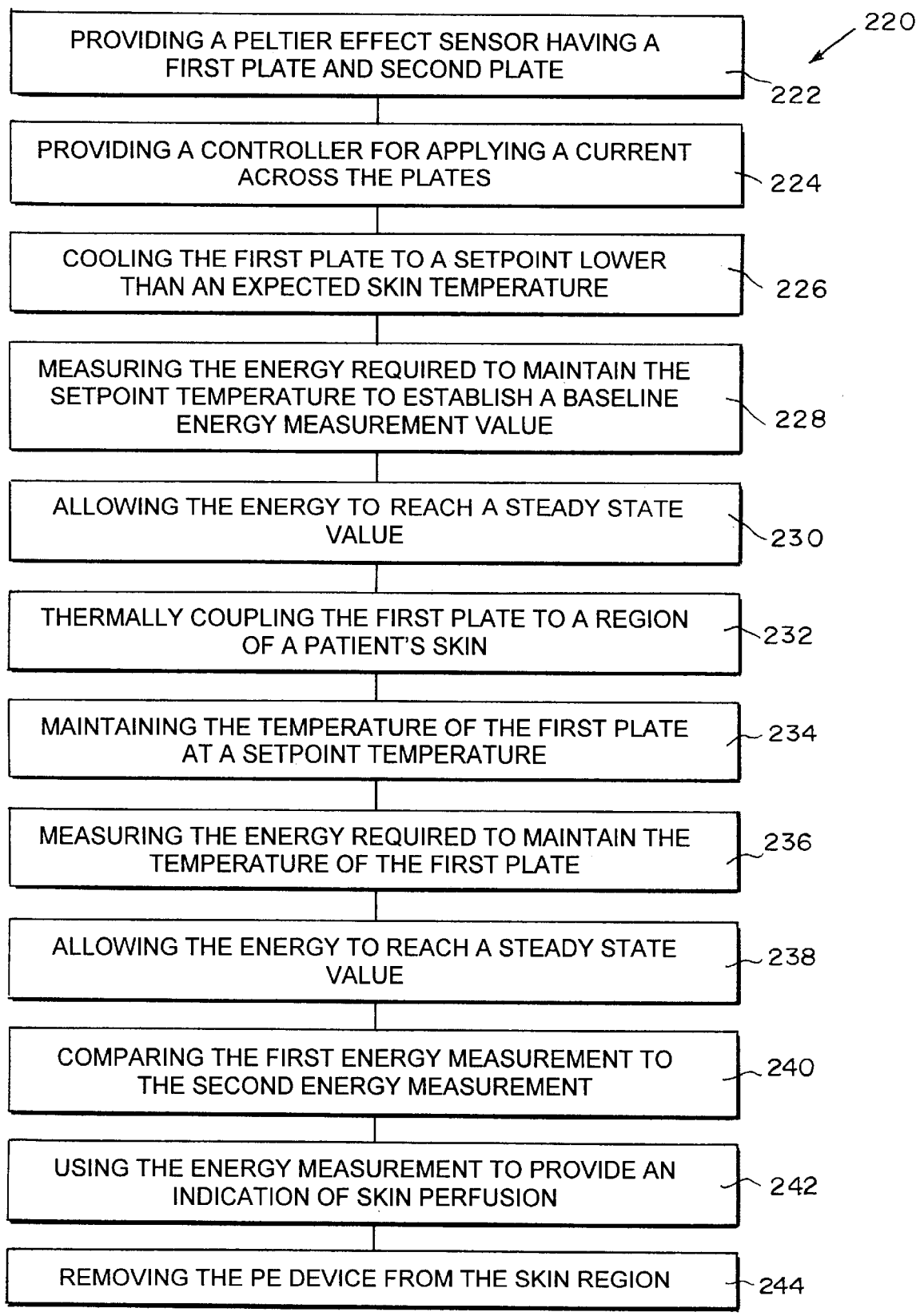

Another embodiment of a method of determining perfusion capacity of a region of a patient's skin 220 is disclosed in FIG. 8. The method 220 includes the step of providing a Peltier Effect Sensor having a first plate spaced apart from a second plate 222. A controller is provided for applying current across the plates 224. The first plate is cooled to a setpoint temperature lower than the expected skin temperature of the region of patient's skin 226. This temperature may be lower than the ambient air temperature if the device 10 disclosed herein is utilized in the method 220. Energy is provided to cool the first plate to the setpoint temperature. The energy required to maintain the first plate at the setpoint temperature is measured to establish a baseline energy measurement value 228. Typically, the baseline energy measurement value is taken when the energy provided has reached a steady state value 230. The first plate of the provided Peltier device is thermally coupled to the region of patient's skin 232. The second plate is placed apart from first plate. After the first plate is placed against the patient's skin, energy is provided to maintain the temperature of the first plate at the setpoint temperature 234. The energy provided to maintain the temperature of the first plate is measured 236. This measurement may be accomplished by measuring the energy value after it has reached a steady state value 238. The first energy measurement is compared to the second energy measurement 240 and these energy measurements are used to provide an indiction of skin perfusion 242. The provided device is then removed from the skin region 244.

While described as using the Peltier effect to determine perfusion capacity, it is within the teaching of the invention to rely upon the Seebeck effect to determine the skin perfusion capacity. Therefore, a method of determining skin perfusion capacity using a first plate and a second plate with a differential temperature therebetween with the plates being juxtaposed and configured such that heat applied to the first plate relative to the second plate will provide an electrical measurement includes the steps of placing the first plate adjacent the patient's skin, measuring an electrical quantity resulting from heat transfer between the patient's skin and first plate and using the measured electrical quantity as an indication of skin perfusion capacity.

A caregiver can use the results of the skin perfusion measurement to provide treatment before bed sores actually begin. The device 10 is a hand held device which is easy to handle and use at any location. The device 10 provides a rapid assessment of skin perfusion. The result of the test is displayed in less than one minute, and preferably less than 30 seconds.

Although the invention has been described in detail with reference to certain preferred embodiments, variations and modifications exist within the scope and spirit of the present invention as described and defined in the following claims.

What is claimed is:

1. A device for determining perfusion capacity in a region of a patient's skin and underlying tissue comprising:
   a thermoelectric device to create a temperature differential,
   a sensor for measuring the temperature differential,
   a controller coupled to the sensor and the thermoelectric device for maintaining the temperature differential substantially constant by providing electrical energy to the thermoelectric device,
   wherein the electrical energy provided to the thermoelectric device when the thermoelectric device is positioned adjacent the region of the patient's skin is indicative of the perfusion capacity.

2. The device of claim 1 wherein the thermoelectric device includes a cold plate and a hot plate, the cold plate and the hot plate having the temperature differential therebetween, and the thermoelectric device is mounted to be positionable adjacent the region of the patient's skin.

3. The device of claim 2 wherein the cold plate is positioned to lie between the region of the patient's skin and the hot plate when the thermoelectric device is positioned adjacent the region of the patient's skin.

4. The device of claim 3 and further comprising a heat sink thermally coupled to the hot plate for maintaining the hot plate at a temperature substantially equal to a temperature of ambient air.

5. The device of claim 1 wherein the thermoelectric device is a Peltier device.

6. The device of claim 1 and further comprising a DC power source electrically coupled to the thermoelectric device.

7. The device of claim 1 and further comprising a gauge for measuring the electrical energy provided to the thermoelectric device.

8. A device for determining a perfusion capacity in a region of a patient's skin and underlying tissue, the device comprising:
   a first plate mounted in a position permitting placement of the first plate adjacent the region of the patient's skin,
   a sensor to determine the temperature of the first plate,
   a controller coupled to the sensor, the controller providing electrical energy to the first plate to maintain the temperature of the first plate substantially constant, and a measuring device measuring the electrical energy provided to the first plate when the first plate is positioned adjacent the region of the patient's skin which measurement is indicative of the perfusion capacity in the region of the patient's skin and underlying tissue.

9. The device of claim 8 and further comprising a gauge coupled to the controller measuring the electrical energy required to maintain the temperature of the first plate substantially constant.

10. The device of claim 8 and further comprising a second plate spaced apart from and thermally coupled to the first plate by a boundary, said second plate being electrically coupled to the controller wherein providing electrical energy to the first and second plate induces heat to cross the boundary between the first plate and the second plate.

11. The device of claim 10 and further comprising a heat sink thermally coupled to the second plate for dissipating heat transferred from the first plate to the second plate.

12. The device of claim 11 wherein the heat sink maintains the temperature of the second plate at a temperature of ambient air surrounding the device.

13. A device for determining a perfusion capacity in a region of a patient's skin and underlying tissue, the device comprising:
   a first plate mounted to be placed in a position adjacent the region of the patient's skin,
   a second plate electrically coupled to the first plate by a junction containing material dissimilar to one of the first and second plates and thermally coupled to the first plate,
   a controller for maintaining the first plate at a first temperature and the second plate at a second temperature, said first and second temperatures defining a temperature differential which is maintained substantially constant by the controller by adjusting electrical energy supplied to the first and second plate, and
   wherein the electrical energy supplied to the first and second plates when the first plate is positioned adjacent the region of the patient's skin is indicative of the perfusion capacity of the region of the patient's skin and underlying tissue.

14. The device of claim 13 further comprising a heat exchanger in thermal communication with the second plate.

15. The device of claim 14 wherein the heat exchanger maintains the second plate at a temperature of ambient air.

16. The device of claim 15 further comprising a fan arranged to force ambient air across the heat exchanger.

17. The device of claim 13 further comprising a power source providing direct current flowing between the first and second plates.

18. The device of claim 17 wherein the polarity of the direct current induces the first plate to have a temperature lower than a temperature of the second plate.

19. The device of claim 18 further comprising a heat exchanger in thermal communication with the second plate.

20. The device of claim 19 wherein the heat exchanger maintains the second plate at a temperature of ambient air.

21. A method for determining a perfusion capacity of a patient's skin and underlying tissue comprising the steps of:
   a) applying a first plate against a region of the patient's skin,
   b) providing energy to dissipate heat absorbed by the first plate from the patient's skin,
   c) measuring the energy required to dissipate heat absorbed by the first plate from the skin,
   d) using the energy measurement to calculate the perfusion capacity,
   wherein the energy provided is electrical energy; and
   further comprising substantially dissipating all of the heat absorbed by the first plate.

22. The method of claim 21 further comprising continuing to provide the energy until the rate at which the energy is provided reaches a steady state value.

23. A method for using a first plate and a second plate and the differential temperature therebetween to determine a perfusion capacity of a region of a patient's skin and underlying tissue, the plates being juxtaposed and configured such that heat applied to the first plate relative to the second plate will provide an electrical measurement, the method comprising the steps of:
   a) placing the first plate adjacent the region of the patient's skin,
   b) providing an electrical measurement indicative of energy affecting the differential temperature, and
   c) providing an indication of the perfusion capacity related to the energy affecting the differential temperature.

24. The method of claim 23 wherein the energy affecting the differential temperature is an energy required to maintain the differential temperature substantially constant.

25. The method of claim 24 further comprising the step of allowing the energy affecting the differential temperature to reach a steady state value after the first plate is placed adjacent the region of the patient's skin.

26. The method of claim 23 further comprising the step of maintaining the second plate at a substantially constant temperature.

27. The method of claim 26 wherein the energy affecting the differential temperature is an energy required to maintain the differential temperature substantially constant.

28. The method of claim 27 further comprising the step of allowing the energy affecting the differential temperature to reach a steady state value after the first plate is placed adjacent the region of the patient's skin.

29. A method for using the Peltier effect (PE) to determine a perfusion capacity of a region of a patient's skin and underlying tissue, the method comprising the steps of:
   a) providing a PE sensor having a first plate to be thermally coupled to the region of the patient's skin and a second plate spaced from the first plate, and a controller for applying a current across the plates,
   b) thermally coupling the first plate to the region of the patient's skin,
   c) measuring the current required to maintain the temperature of the first plate at a setpoint temperature, and
   d) using the current measurement to provide an indication of the perfusion capacity.

30. The method of claim 29 and further comprising the step of cooling the first plate to the setpoint temperature which is lower than an expected temperature of the region of the patient's skin by applying a current to the plates prior to thermally coupling the first plate to the region of the patient's skin.

31. The method of claim 30 and further comprising the step of measuring the current required to maintain the temperature of the first plate at the setpoint temperature to determine a baseline current value prior to thermally coupling the first plate to the region of the patient's skin.

32. The method of claim 31 and further comprising the steps of permitting the measured current to reach a substantially steady state value after thermally coupling the first plate to the region of the patient's skin and comparing the substantially steady state value of the measured current to the baseline current value to provide an indication of perfusion capacity.

33. The method of claim 32 and further comprising the step of maintaining the thermal coupling of the first plate to the region of the patient's skin until the substantially steady state current value is compared to the baseline current value.

* * * * *